(12) United States Patent
Govari

(10) Patent No.: US 7,575,550 B1
(45) Date of Patent: Aug. 18, 2009

(54) POSITION SENSING BASED ON ULTRASOUND EMISSION

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/265,715

(22) Filed: Mar. 11, 1999

(51) Int. Cl.
*A61B 8/00* (2006.01)

(52) U.S. Cl. .................. 600/437; 600/424; 600/443

(58) Field of Classification Search ............. 600/424, 600/437, 443–447
See application file for complete search history.

(56) References Cited

U.S. PATENT DOCUMENTS

| | | | |
|---|---|---|---|
| 3,644,825 A | 2/1972 | Davis, Jr. et al. | 324/41 |
| 3,713,133 A | 1/1973 | Nathans | 340/280 |
| 3,868,565 A | 2/1975 | Kuipers | 324/34 R |
| 4,017,858 A | 4/1977 | Kuipers | 343/100 R |
| 4,054,881 A | 10/1977 | Raab | 343/112 R |
| 4,173,228 A | 11/1979 | Van Steenwyk et al. | |
| 4,317,078 A | 2/1982 | Weed et al. | 324/208 |
| 4,407,296 A | 10/1983 | Anderson | |
| 4,485,813 A | 12/1984 | Anderson et al. | |
| 4,560,930 A | 12/1985 | Kouno | 324/207 |
| 4,613,866 A | 9/1986 | Blood | 343/448 |
| 4,642,786 A | 2/1987 | Hansen | 364/559 |
| 4,651,436 A | 3/1987 | Gaal | 33/533 |
| 4,710,708 A | 12/1987 | Rorden et al. | 324/207 |
| 4,807,202 A | 2/1989 | Cherri et al. | 367/129 |
| 4,815,469 A | 3/1989 | Cohen et al. | |
| 4,846,191 A | 7/1989 | Brockway et al. | |
| 4,849,692 A | 7/1989 | Blood | 324/208 |
| 4,905,698 A | 3/1990 | Strohl, Jr. et al. | 128/653 R |
| 4,917,095 A | 4/1990 | Fry et al. | 128/660.03 |
| 4,945,305 A | 7/1990 | Blood | 324/207.17 |
| 4,967,755 A | 11/1990 | Pohndorf | |
| 5,002,137 A | 3/1991 | Dickinson et al. | 175/19 |

(Continued)

FOREIGN PATENT DOCUMENTS

DE     3011671     10/1981

(Continued)

OTHER PUBLICATIONS

Weir, R.F. et al: "A Portable, Real-Time, Clinical Gait Velocity Analysis System"; IEEE Transactions on Rehabilitation Engineering, US, IEEE Inc., New York; vol. 5, No. 4, Dec. 1997; pp. 310-320.

(Continued)

*Primary Examiner*—Eric F Winakur
*Assistant Examiner*—Michael Rozanski
(74) *Attorney, Agent, or Firm*—Louis J. Capezzuto

(57) ABSTRACT

An Apparatus for determining the disposition of an object relative to a reference frame includes at least one field generator, which generates an electromagnetic field in a vicinity of the object and at least one transducer, which is fixed to the object. The at least one transducer vibrates at a predetermined vibrational frequency and emits energy, responsive to an interaction of the electromagnetic field therewith. One or more detectors in a vicinity of the object are also utilized to detect the energy emitted by the transducer and generate signals in response thereto. A signal processor is also included for receiving and processing the detector signals to determine coordinates of the object.

29 Claims, 11 Drawing Sheets

U.S. PATENT DOCUMENTS

| | | | |
|---|---|---|---|
| 5,042,486 A | 8/1991 | Pfeiler et al. | 128/653 R |
| 5,057,095 A * | 10/1991 | Fabian | 128/899 |
| 5,068,608 A | 11/1991 | Clark, Jr. | 324/220 |
| 5,078,144 A | 1/1992 | Sekino et al. | 128/660.03 |
| 5,099,845 A | 3/1992 | Besz et al. | 128/653.1 |
| 5,172,056 A | 12/1992 | Voisin | 324/207.17 |
| 5,201,715 A | 4/1993 | Masters | |
| 5,211,165 A | 5/1993 | Dumoulin et al. | 128/653.1 |
| 5,215,680 A | 6/1993 | D'Arrigo | 252/307 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,265,610 A | 11/1993 | Darrow et al. | 128/653.1 |
| 5,269,289 A | 12/1993 | Takehana et al. | 128/4 |
| 5,273,025 A | 12/1993 | Sakiyama et al. | 128/6 |
| 5,275,166 A | 1/1994 | Vaitekunas et al. | 128/660.03 |
| 5,295,486 A | 3/1994 | Wollschlager et al. | 128/661.01 |
| 5,309,913 A | 5/1994 | Kormos et al. | 128/653.1 |
| 5,325,873 A | 7/1994 | Hirschi et al. | 128/899 |
| 5,330,520 A | 7/1994 | Maddison et al. | |
| 5,353,354 A | 10/1994 | Keller et al. | |
| 5,353,800 A | 10/1994 | Pohndorf et al. | |
| 5,375,596 A | 12/1994 | Twiss et al. | 128/653.1 |
| 5,377,678 A | 1/1995 | Dumoulin et al. | 128/653.1 |
| 5,383,874 A | 1/1995 | Jackson et al. | 606/1 |
| 5,391,199 A | 2/1995 | Ben-Haim et al. | 607/122 |
| 5,404,877 A | 4/1995 | Nolan et al. | |
| 5,412,619 A | 5/1995 | Bauer | 367/128 |
| 5,425,367 A | 6/1995 | Shapiro et al. | 128/653.1 |
| 5,425,382 A | 6/1995 | Golden et al. | 128/899 |
| 5,429,132 A | 7/1995 | Guy et al. | 128/653.1 |
| 5,437,277 A | 8/1995 | Dumoulin et al. | 128/653.1 |
| 5,443,489 A | 8/1995 | Ben-Haim | 607/115 |
| 5,453,687 A | 9/1995 | Zierdt et al. | 324/207.17 |
| 5,456,718 A * | 10/1995 | Szymaitis | 128/899 |
| 5,471,988 A | 12/1995 | Fujio et al. | 128/660.03 |
| 5,513,636 A | 5/1996 | Palti | |
| 5,522,869 A | 6/1996 | Burdette et al. | 607/97 |
| 5,549,638 A | 8/1996 | Burdette | 607/97 |
| 5,558,091 A | 9/1996 | Acker et al. | 128/653.1 |
| 5,558,092 A | 9/1996 | Unger et al. | 128/660.03 |
| 5,566,676 A | 10/1996 | Rosenfeldt et al. | |
| 5,577,502 A | 11/1996 | Darrow et al. | 128/653.1 |
| 5,617,857 A | 4/1997 | Chader et al. | 128/653.1 |
| 5,622,169 A | 4/1997 | Golden et al. | 128/653.1 |
| 5,636,644 A | 6/1997 | Hart et al. | |
| 5,645,065 A | 7/1997 | Kay et al. | |
| 5,682,886 A | 11/1997 | Delp et al. | 128/653.1 |
| 5,689,576 A | 11/1997 | Schneider et al. | |
| 5,690,113 A | 11/1997 | Sliwa | |
| 5,694,945 A | 12/1997 | Ben-Haim | 128/736 |
| 5,697,377 A | 12/1997 | Wittkampf | 128/696 |
| 5,715,822 A | 2/1998 | Watkins et al. | 128/653.5 |
| 5,727,552 A * | 3/1998 | Ryan | 128/899 |
| 5,729,129 A | 3/1998 | Acker | 324/207.12 |
| 5,743,267 A | 4/1998 | Nikolic et al. | |
| 5,752,513 A | 5/1998 | Acker et al. | 128/653.1 |
| 5,762,066 A | 6/1998 | Law et al. | |
| 5,762,609 A | 6/1998 | Benaron et al. | |
| 5,769,843 A | 6/1998 | Abela et al. | 606/10 |
| 5,797,849 A | 8/1998 | Vesely et al. | 600/461 |
| 5,798,693 A | 8/1998 | Engellenner | |
| 5,817,022 A | 10/1998 | Vesely | |
| 5,868,673 A | 2/1999 | Vesely | |
| 5,913,820 A | 6/1999 | Bladen et al. | |
| 5,928,137 A | 7/1999 | Green | |
| 5,964,709 A | 10/1999 | Chiang et al. | |
| 5,999,857 A | 12/1999 | Weijand et al. | |
| 6,021,352 A | 2/2000 | Christopherson et al. | |
| 6,026,818 A | 2/2000 | Blair et al. | |
| 6,053,873 A | 4/2000 | Govari et al. | |
| 6,073,043 A | 6/2000 | Schneider | |
| 6,076,007 A * | 6/2000 | England et al. | 128/899 |
| 6,140,740 A | 10/2000 | Porat et al. | |
| 6,141,293 A | 10/2000 | Amorai-Moriya et al. | |
| 6,159,156 A | 12/2000 | Van Bockel | |
| 6,161,032 A | 12/2000 | Acker | |
| 6,172,499 B1 | 1/2001 | Ashe | |
| 6,198,983 B1 | 3/2001 | Halm | |
| 6,206,835 B1 | 3/2001 | Spillman, Jr. et al. | |
| 6,223,066 B1 | 4/2001 | Govari | |
| 6,226,547 B1 | 5/2001 | Lockhart et al. | |
| 6,237,398 B1 | 5/2001 | Porat et al. | |
| 6,239,724 B1 | 5/2001 | Doron et al. | |
| 6,270,458 B1 | 8/2001 | Barnea | |
| 6,305,381 B1 | 10/2001 | Weijand et al. | |
| 6,332,089 B1 * | 12/2001 | Acker et al. | 128/899 |
| 6,347,241 B2 | 2/2002 | Burbank et al. | |
| 6,373,240 B1 | 4/2002 | Govari | |
| 6,380,732 B1 | 4/2002 | Gilboa | |
| 6,490,474 B1 | 12/2002 | Willis et al. | |
| 6,638,231 B2 | 10/2003 | Govari et al. | |
| 6,788,967 B2 | 9/2004 | Ben-Haim et al. | |
| 6,875,179 B2 | 4/2005 | Ferguson et al. | |
| 7,160,258 B2 | 1/2007 | Imran et al. | |
| 7,174,201 B2 | 2/2007 | Govari et al. | |
| 2001/0018594 A1 | 8/2001 | Kreg | |
| 2001/0051766 A1 | 12/2001 | Gazdzinski | |
| 2002/0107445 A1 | 8/2002 | Govari | |
| 2003/0023161 A1 | 1/2003 | Govari et al. | |
| 2003/0120150 A1 | 6/2003 | Govari | |
| 2004/0015075 A1 | 1/2004 | Kimchy et al. | |
| 2004/0015079 A1 | 1/2004 | Berger et al. | |

FOREIGN PATENT DOCUMENTS

| | | |
|---|---|---|
| DE | 100 03 338 A | 11/2000 |
| EP | 0021451 | 1/1981 |
| EP | 0053976 | 6/1982 |
| EP | 0646365 | 4/1995 |
| EP | 0897690 | 2/1999 |
| EP | 1004267 | 5/2000 |
| EP | 1 034 736 A | 9/2000 |
| JP | 60-70324 | 4/1985 |
| JP | H08-015489 B2 | 2/1996 |
| JP | 08-313622 | 11/1996 |
| WO | WO 83 02053 A | 6/1983 |
| WO | WO 83/03348 | 10/1983 |
| WO | WO 92/03090 | 3/1992 |
| WO | WO 94/04938 | 3/1994 |
| WO | WO 94/23647 | 10/1994 |
| WO | WO 96/05768 | 2/1996 |
| WO | WO 96/41119 | 12/1996 |
| WO | WO 97/29678 | 8/1997 |
| WO | WO 97/29701 | 8/1997 |
| WO | WO 97/29709 | 8/1997 |
| WO | WO 97/29710 | 8/1997 |
| WO | WO 97/32179 | 9/1997 |
| WO | WO 97/33513 | 9/1997 |
| WO | WO 98/11840 | 3/1998 |
| WO | WO 98/36236 | 8/1998 |
| WO | WO 99 27837 A | 6/1999 |
| WO | WO 99/34453 | 7/1999 |
| WO | WO 99/34731 | 7/1999 |
| WO | WO 99 51143 A | 10/1999 |
| WO | WO 00/16686 | 3/2000 |
| WO | WO 00/32092 | 6/2000 |
| WO | WO 01/36014 | 5/2001 |
| WO | WO 01 64109 A | 9/2001 |
| WO | WO 02 39917 A | 5/2002 |

OTHER PUBLICATIONS

EPO Search Report dated Oct. 14, 2003 for EPO Application No. EP 03 25 3786.

EPO Search Report dated Oct. 13, 2003 for EPO Application No. EP 03 25 3784.

EPO Search Report dated Oct. 13, 2003 for EPO Application No. 03 25 3785.

EPO Search Report dated Dec. 4, 2003 for EPO Application No. 02 25 8960.

U.S. Patent No. 5,864,709, filed Oct. 12, 1999, Chiang et al.

EPO Search Report dated Mar. 19, 2002 re: EP01310521.

EPO Search Report dated Oct. 13, 2003 re: EP03253784.

EPO Search Report dated Oct. 14, 2003 re: EP03253786.

Biosense Inc., Pending USSN 09/265715.

Biosense Inc. 10/029595.

Biosense Inc. 10/029473.

Chakko et al 'Clinical, Radiographic and Hemodynamic Correlations in Chronic Congestive Heart Failure: Conflicting Results May Lead to Inappropriate Care' AJM (1991) 90(3) pp. 353-359.

Dargie, H.J., et al 'Fortnightly Review: Diagnosis and Management of Heart Failure' BMJ 1994 308 pp. 321-8.

Ohlsson A et al 'Continuous Ambulatory Haemodynamic Monitoring with an Implantable System' European Heart Journal (1998) 19(1) pp. 174-184.

Steinhaus D.M. et al 'Initial Experience with an Implantable Hemodynamic Monitor' Circulation (1996) 93(4) pp. 745-752.

Stevenson LW et al 'Poor Survival of Patients with Idopathic Cardiomyopathy Considered Too Well for Transplantation' AJM (1987) 83(5) pp. 871-876.

Stevenson, LW 'Tailored Therapy Before Transplantation for Treatment of Advanced Heart Failure: Effective Use of Vasodilators and Diuretics' J Heart Lung Transplant (1991) 10 pp. 468-76.

Stevenson, LW et al 'The LimitedReliability of Physical Signs for Estimating Hemodynamics in Chronic Heart Failure' JAMA (1989) 261 pp. 884-888.

* cited by examiner

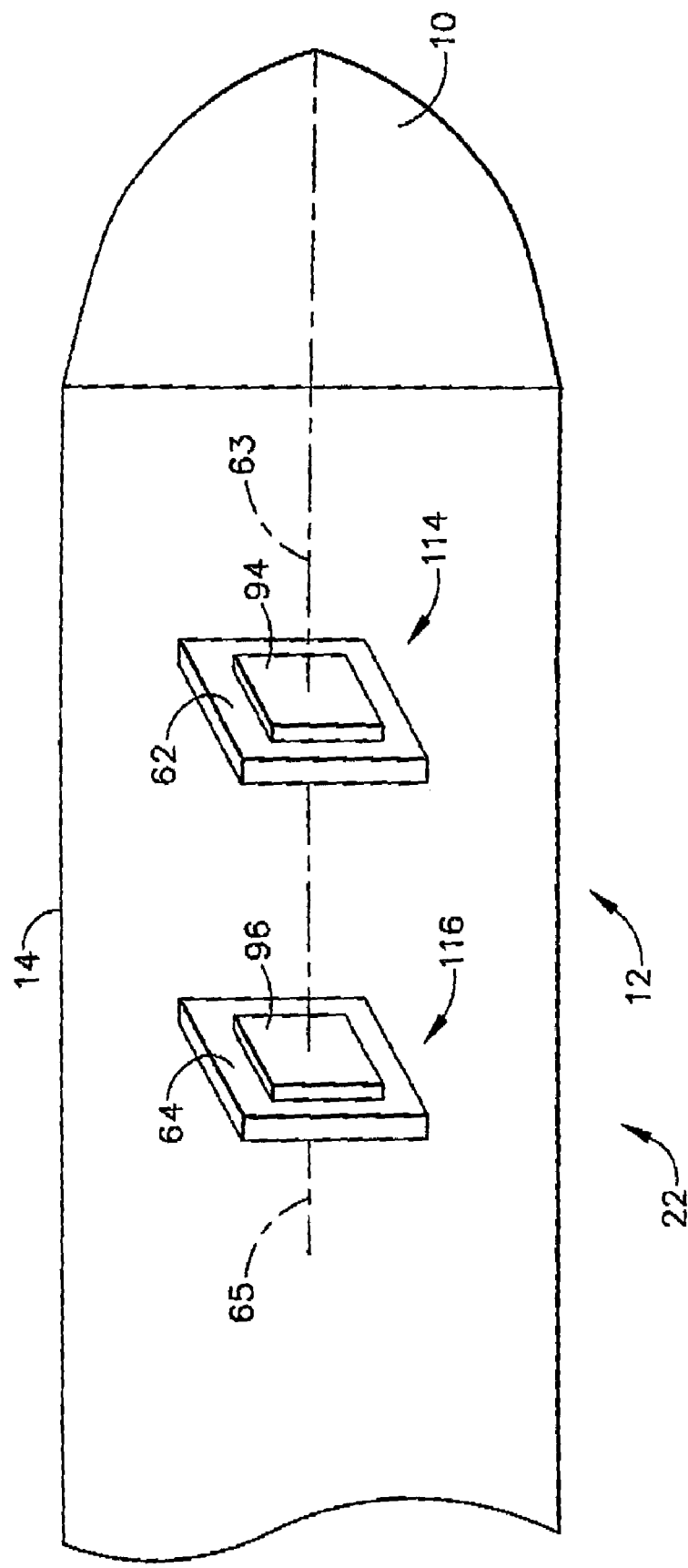

POSITION SENSING BASED ON ULTRASOUND EMISSION

FIELD OF THE INVENTION

The present invention relates generally to position sensing systems and specifically to systems for determining the position of an object inside a human body.

BACKGROUND OF THE INVENTION

In many medical procedures, probes, such as endoscopes and catheters, are inserted into a patient's body. Various methods of determining the location of these inserted medical devices are known in the art. X-ray imaging is the most commonly used location confirmation system. Position determining systems can also be used for this purpose.

Ultrasound intrabody position sensing is well known. Some such systems require an active transducer in the catheter, generally at or adjacent the distal end of the catheter, connected by wires to a console outside the body. The transducer either receives ultrasonic waves from emitters outside the body or radiates ultrasonic waves to receivers outside the body. Other ultrasonic systems use a passive ultrasound reflector in the catheter which gives a strong reflection of ultrasonic waves irradiating the body without the necessity of running wires through the catheter. These passive systems necessarily create a strong background of ultrasonic radiation against which the position of the reflector must be found.

U.S. Pat. No. 3,713,133 to Nathans, whose disclosure is incorporated herein by reference, describes a theft-prevention system in which a piezoelectric crystal having a resonant frequency is incorporated into a device which is then attached to individual items within a store. When a radio frequency (RF) signal having a frequency equal to the resonant frequency of the crystal strikes the crystal, an oscillating electrical field gradient is produced across the face of the crystal at the radiated RF frequency, and two tin foil members mounted on the crystal vibrate, emitting ultrasound. Detection of the ultrasound under appropriate conditions produces an alarm, indicative of an attempt to remove the item from the store without authorization.

U.S. Pat. No. 3,713,133 also describes a small, thin metal diaphragm having a resonant vibrational frequency. When the diaphragm is irradiated with an ultrasound field at or near the resonant frequency, the diaphragm vibrates at that frequency. An RF field also irradiates the diaphragm at a substantially higher frequency, and the vibration of the diaphragm induced by the ultrasound field modulates the RF field. This modulation is detected by an RF transducer, which activates an alarm. These systems do not provide specific information describing the location of the item, but only that the item has entered a detection area (typically near an exit from the store).

PCT Patent Publication WO 96/05768 to Ben-Haim et al., whose disclosure is incorporated herein by reference, describes a locating system for determining the location and orientation of an invasive medical instrument whereby an externally applied RF field induces a current in three coils located within the invasive medical instrument. Wires or some other form of physical leads are required to carry this induced signal from the catheter to a signal processor in the extrabody space. The processor analyzes the signal so as to calculate the location and orientation of the invasive medical instrument.

U.S. Pat. No. 5,522,869 to Burdette et al., and U.S. Pat. No. 5,549,638 to Burdette, whose disclosures are incorporated herein by reference, describe an ultrasound device for use in a thermotherapy apparatus to treat cancer. To operate this device, ultrasound transducers are arranged in a cylindrical shape around the treatment site, and are activated by radio frequency power. The resultant ultrasound waves heat tissue within the treatment site, thereby producing the desired therapeutic effect. The output of this device is therefore heat, and there is no indication of the location or orientation of the individual ultrasound transducers.

U.S. Pat. No. 5,325,873 to Hirschi et al., whose disclosure is incorporated herein by reference, describes a system to verify the location of a tube or other object inserted into the body. It incorporates a resonant electrical circuit attached to the object which resonates upon stimulation by a hand-held RF transmitter/receiver external to the body. The electromagnetic field generated due to resonance of the circuit is detected by the hand-held device, which subsequently turns on a series of LEDs to indicate to the user the direction to the target. An additional visual display indicates when the transmitter/receiver is directly above the object.

U.S. Pat. No. 5,412,619 to Bauer, whose disclosure is incorporated herein by reference, describes a system for tracking the three-dimensional position of a moving object. At least three ultrasound transmitters in known positions send signals which are detected by receiving stations mounted on the moving object. At each station, the detected signals are encoded into a form suitable for radio transmission, and a radio transmitter passes the information to a computer which determines the location of the object through a triangulation algorithm. The system in U.S. Pat. No. 5,412,619 is primarily suitable to be attached to the exterior of the human body to allow determination of gross body positions and movements.

U.S. Pat. No. 4,807,202 to Cherri et al, whose disclosure is incorporated herein by reference, comprises a visual environment simulator in which three separately positioned ultrasonic transmitters send signals to each of three ultrasonic receivers in order to monitor the change in the spatial coordinates and the orientation angles of the viewer and/or mobile unit carrying the viewer.

SUMMARY OF THE INVENTION

It is an object of the present invention to provide an improved ultrasonic object tracking system.

It is a further object of some aspects of the present invention to provide a catheter location system which is based on ultrasound emission from the catheter's distal end and which does not require a wired connection to the distal end.

Preferred embodiments of the present invention are based on the interaction of electromagnetic (RF) and ultrasonic energy fields. An RF-responsive transducer, having a resonant vibrational frequency in the ultrasonic range, is fixed to an object and is irradiated with an RF energy field. The transducer is induced to vibrate and emits energy, either RF or ultrasonic energy, or both, responsive to an interaction of the RF field with the vibration. The emitted energy is detected and is used to determine position and/or orientation coordinates of the object.

In some preferred embodiments of the present invention, the transducer emits ultrasonic waves responsive to the RF field impinging thereon. The emitted ultrasound waves are detected by a plurality of ultrasound detectors, preferably three or more. A processor receives signals from the ultrasound detectors and processes them to determine the position and/or orientation of the object, using triangulation, time-of-flight measurement, or other suitable methods of position determination, as are known in the art. There is preferably no wired connection between the transducer and the detectors, the processor or any other elements of the apparatus.

In some of these preferred embodiments, the transducer comprises one or more piezoelectric crystals, each having a respective resonant frequency, and one or more foil members coupled to each crystal. Although in the preferred embodiments described herein, the transducer comprises foil members, it is understood that other conductive materials could also be used. One or more RF radiators generate RF signals at or near each of the resonant frequencies in a vicinity of the crystals, causing the foil members to vibrate and emit ultrasound waves at a characteristic frequency for each crystal/foil unit.

In a preferred embodiment of the present invention, the transducer comprises three crystal/foil units, having respective, mutually substantially orthogonal axes. Each unit is constructed and mounted such that its resonant frequency is different from that of the other two units. In this embodiment, the RF generators generate fields at each of the three resonant frequencies, either simultaneously or in a continuous cycle through the three frequencies. Using methods known in the art, some of which are described, for example, in PCT patent publication WO 96/05768, the three components of the angular orientation vector of the object, as well as the three position vector components, are then calculated based on the signals from the ultrasound detectors.

Although the anti-theft system described in the above referenced U.S. Pat. No. 3,713,133 uses radio frequency (RF) irradiation to produce ultrasonic emission in a manner similar to the present invention, the anti-theft system is capable only of reporting the presence or absence of a target, and cannot be used to locate and track an object.

In some preferred embodiments of the invention, the transducer is incorporated into an invasive medical instrument such as a catheter, endoscope, trocar, or laparoscope. In one of these preferred embodiments, the transducer is fixed to the distal end of a trocar through which a laparoscope is passed in abdominal surgery. The position of the distal end is determined so as to prevent injury to underlying bowel and blood vessels, in particular the common iliac vein. In another preferred embodiment, the location of the distal end of a Swan-Ganz catheter being inserted into the internal jugular vein is continuously monitored in order to decrease the likelihood of puncture injury of the carotid artery or the pleural cavity.

In still another preferred embodiment, the precise placement of a stent into the descending aortic artery in treatment of an aortic aneurysm is made possible by incorporating one or more transducers units into the distal end of the catheter placing the stent. In this embodiment, knowing the angular orientation of the catheter is important in addition to knowing its spatial location because of the need to avoid placing the stent in a manner which blocks the lumbar arteries supplying the spinal cord. Furthermore, since there is no wired connection needed between the transducers and other elements of the position sensing system, one or more of the transducers could be fixed to the stent and used to determine its position and orientation before, during and after placement by the catheter. The use of stents incorporating wireless transducers is described further in PCT patent application PCT/IL97/00447, which is assigned to the assignee of the present patent application and is incorporated herein by reference.

In a further preferred embodiment of the present invention, one or more of the transducers are incorporated in a probe designed to destroy a tumor, thereby allowing the physician to know the precise location and orientation of the probe with respect to known coordinates of the tumor. A particular application of this preferred embodiment is the removal of a pituitary tumor by heat, cold, or other means. Surgical probes using position sensors are described, for example, in the following PCT patent applications: PCT/US97/022443, PCT/IL97/00058 and PCT/IL97/00059, which are incorporated herein by reference.

In distinction to active ultrasound-based position-sensing systems known in the art, in the present invention ultrasound waves are generated passively at the probe. This method of ultrasound generation is advantageous because there is no need for wires leading from the probe to either an outside power source (as in U.S. Pat. No. 5,412,619) or to signal amplifiers and a signal processor (as in patent publication WO 96/05768 and U.S. Pat. No. 4,807,202). An additional advantage of the passive generation of ultrasound in this invention compared to some other currently used methods is that there is no potentially disruptive background ultrasound radiation created by irradiation from outside the body. Ultrasound radiation at the resonant frequency comes only from the transducer, typically from the crystal/foil unit described above. An advantage deriving from the unit's very small size, as well as from the lack of additional hardware required within the probe, is that the invasive medical instrument can be made small and flexible compared to other types of emitters and detectors used in position sensing systems known in the art. Additionally, the use of such a probe in an invasive medical instrument obviates exposure of the patient to potentially harmful ionizing radiation which is often used to determine the location of an instrument within the patient's body.

In other preferred embodiments of the present invention, the transducer comprises a diaphragm which vibrates at the resonant frequency. Using methods similar to those described in U.S. Pat. No. 3,713,133, such as the embodiment shown in FIG. 4 thereof, ultrasound with a frequency substantially similar to the resonant frequency of the diaphragm is generated by an ultrasound generator at a known location and is directed towards a vicinity of the transducer. The diaphragm mechanically vibrates at its resonant frequency in response to the externally applied ultrasound radiation. A radio frequency (RF) field of substantially higher frequency is initially generated in a vicinity of the sensor either before or at substantially the same time as the time when the ultrasound field is initiated. A portion of the RF radiation is modulated responsive to the mechanical vibration of the diaphragm. The modulated RF signal is detected by an RF detector and is used to determine the position of the object.

In U.S. Pat. No. 3,713,133, detection of the modulated RF signal is used to trigger an alarm indicating that the presence of a diaphragm has been detected. No additional information is derived from the modulated RF signal. In accordance with a preferred embodiment of the present invention, the radiated and detected RF and ultrasound signals are used to calculate the location of the diaphragm, as described hereinbelow. A time period starting from the initiation of ultrasound field generation and ending when a modulated RF signal is first detected at the RF detector is substantially the same as the "time of flight" which ultrasound takes to traverse the distance from the ultrasound generator to the diaphragm. A signal processor calculates the distance from the ultrasound generator to the diaphragm based on the measured "time of flight" and the speed of sound in tissue. Repeating this process using, in sequence, two or more additional ultrasound generators at known points in space yields the distance from the diaphragm to three known points, and allows the signal processor to calculate the location of the object with respect to an external reference frame.

In some additional preferred embodiments of the present invention, three non-collinear diaphragms are fixed at known positions to the object, each diaphragm having a substantially different resonant frequency from that of the other diaphragms. The location of each diaphragm is found using the procedure described above, this calculation thereby yielding the angular orientation of the sensor.

The present invention will be more fully understood from the following detailed description of the preferred embodiments thereof, taken together with the drawings, in which:

BRIEF DESCRIPTION OF THE DRAWINGS

FIG. 2C is a schematic illustration of the distal end of a catheter, for use in the system of FIG. 1, in accordance with another preferred embodiment of the present invention;

DETAILED DESCRIPTION OF PREFERRED EMBODIMENTS

Figure 1:
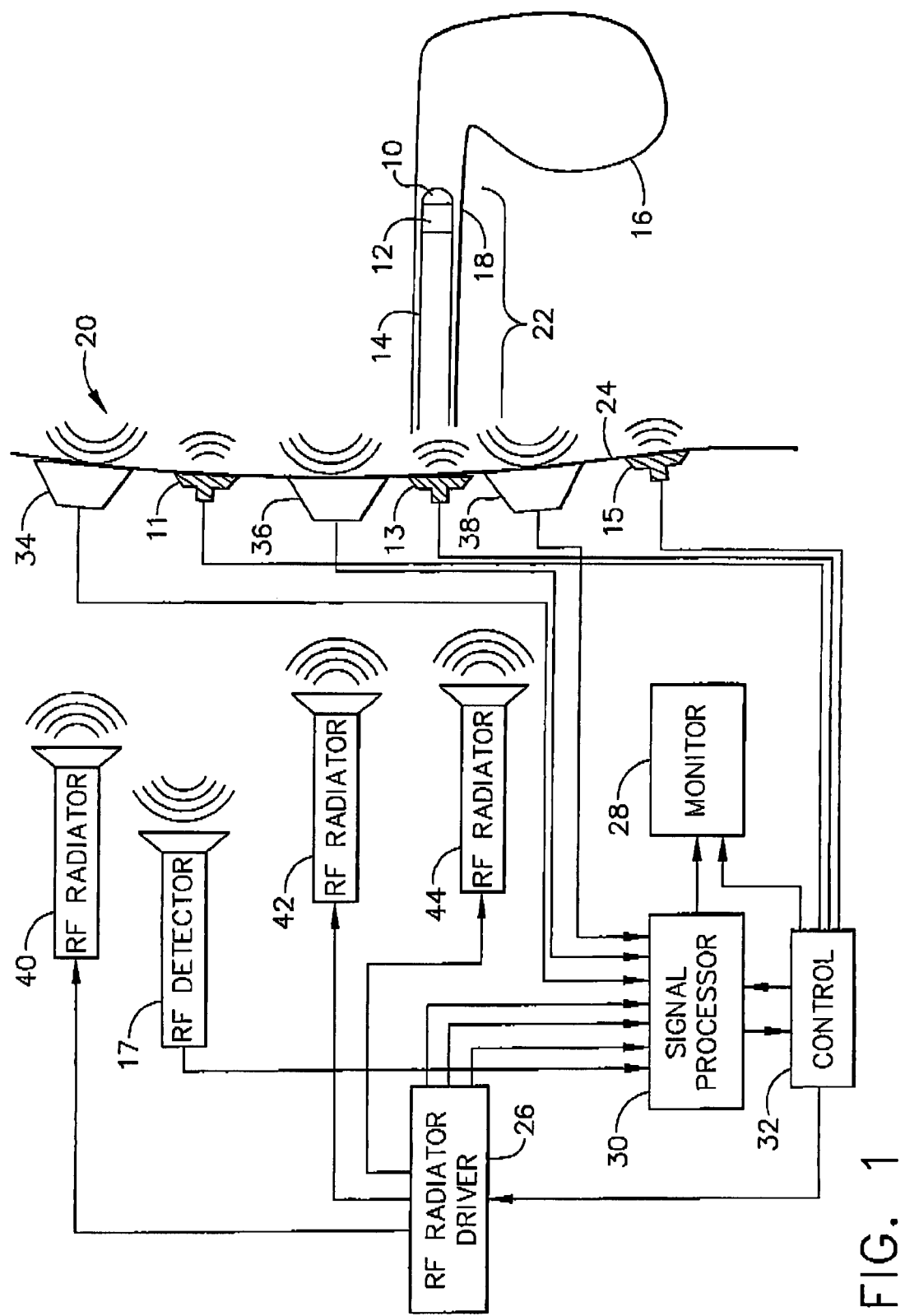
FIG. 1 is a schematic illustration of a catheter tracking system, in accordance with a preferred embodiment of the present invention.

FIG. 1 is a schematic representation of a system 20 for tracking the position of a catheter 22 in the body of a human or non-human subject, in accordance with a preferred embodiment of the present invention. In this application, catheter 22 is inserted through a blood vessel 18 of a patient using standard techniques. Catheter 22 comprises a body 14, a locating transducer 12, and an active portion 10 at the distal end of the catheter. The active portion, in accordance with various preferred embodiments of the invention, may include an electrical sensor, an ultrasound head, a fiber optic viewing head, an electrical stimulator, an electrical or laser ablator, an ionic sensor, an oxygen or carbon dioxide sensor, an accelerometer, a blood pressure or temperature sensor, or a cryogenic probe, as are known in the art. In general, the catheter will include leads, light guides, wave guides, etc., for energizing the active portion in response to commands of an operator, and may also include a tip deflection mechanism, for steering the catheter inside the body.

The position and/or orientation of the distal end of the catheter is obtained by determining the position and/or orientation of transducer 12, which preferably comprises from one to three crystal/foil units, such as those shown below in FIGS. 2A, 2C, and 3A. Such units resonate and emit ultrasonic radiation when subjected to RF irradiation of an appropriate frequency, as described in U.S. Pat. No. 3,713,133, particularly with reference to FIG. 4B thereof.

The RF radiation is initiated by control signals from a control unit 32 which cause an RF radiator driver 26 to generate driving signals. The driving signals in turn cause one or more RF radiators 40, 42 and 44 located outside a body surface 24 of the patient to emit RF radiation. A representation of the driving signals is also sent to a signal processor 30. The ultrasonic radiation from locating transducer 12, generated by one or more resonating crystal/foil units, is detected by a plurality of ultrasound detectors 34, 36, and 38. Other elements shown in FIG. 1, such as ultrasound generators 11, 13 and 15, are described below with reference to other embodiments of the present invention.

The detectors are arranged such that signal processor 30 can utilize inputs comprising the representation of the driving signals and measurements from detectors 34, 36, and 38 in performing a triangulation algorithm, as is known in the art, in order to calculate the position of locating transducer 12. Detectors 34, 36, and 38 may be arranged in any convenient position and orientation, but it is preferable that (a) they are fixed in respect to some reference frame; (b) they are non-overlapping, that is, there are no two detectors with the exact, identical location and orientation; (c) the detectors are not placed collinearly; and (d) two detectors and the locating transducer are at no time all collinear.

It should be understood that placement of detectors 34, 36, and 38 and the number of resonating units to be incorporated in the locating transducer 12 will vary according to each application of the invention. In particular, some preferred applications of the present invention require precise knowledge of the orientation of the catheter (e.g. laser ablation), while others only require knowledge of the position of the catheter (e.g. gastrointestinal tract tube placement).

The ultrasonic signals generated by transducer 12 are transduced by detectors 34, 36, and 38, into electrical signals which are passed to signal processor 30, in either analog or digital form. Signal processor 30 processes the outputs of the detectors to calculate the position and/or orientation of the locating transducer 12, and transmits this information to a display monitor 28 and/or control unit 32.

In practice, the active end of the catheter may be used to gather information, such as ultrasound echo information, electrical activity information, etc., and optionally to perform certain procedures on the arteries (or veins) or other tissue within an organ chamber 16 to which the artery (or vein) leads. Particular examples of organ chambers are the chambers of the heart, brain, or gastrointestinal tract.

Figure 2A:
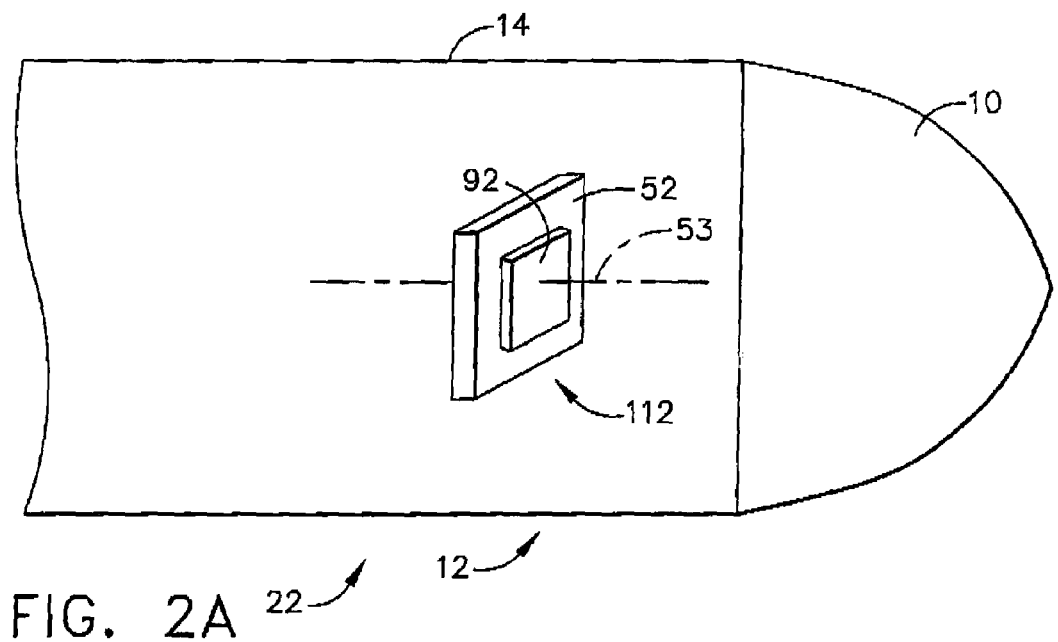
FIG. 2A is a schematic illustration of the distal end of a catheter, for use in the system of FIG. 1, in accordance with a preferred embodiment of the present invention.
Figure 2B:
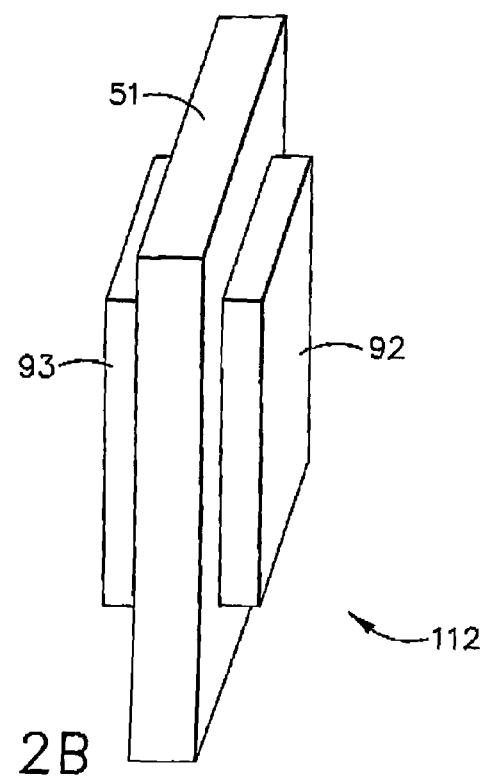
FIG. 2B is a schematic illustration of a transducer, for use in the system of FIG. 1, in accordance with a preferred embodiment of the present invention.

Reference is now made to FIGS. 2A, and 2B. FIG. 2A is a schematic illustration of the distal end of catheter 22, in accordance with a preferred embodiment of the present invention. In this preferred embodiment, transducer 12 comprises a crystal/foil unit 112, shown in detail in FIG. 2B, which comprises a piezoelectric crystal 52 and foil members 92 and 93 coupled to crystal 52. Crystal/foil unit 112 is mounted in catheter body 14 such that an axis 53 of unit 112 is parallel to a longitudinal axis of the catheter. As described in the above-mentioned U.S. Pat. No. 3,713,133, the RF field produced by RF radiator 40 causes ultrasonic resonance in crystal/foil unit 112. Radiators 42 and 44 generally need not be utilized in this preferred embodiment. In response to the RF field, unit 112 emits acoustic radiation, which is detected by detectors 34, 36, and 38, each of which sends signals corresponding thereto to signal processor 30.

The signal processor preferably uses the initiation time of the driving signal to RF radiator 40, the time of arrival at each detector of the acoustic radiation from unit 112, and the speed of sound in tissue, in order to determine the distances from the unit 112 to each of the detectors. The initiation time of a driving signal is substantially the same time as that when acoustic radiation leaves a crystal/foil unit, so the signal processor calculates the "time of flight" of acoustic radiation from unit 112 to each of the detectors, and multiplies each of these times by the speed of sound in tissue to yield the distances from unit 112 to each detector. With these distances, signal processor 30 calculates three-dimensional position coordinates of transducer 12 with respect to a reference frame, using methods known in the art.

FIG. 2C is a schematic illustration of the distal end of catheter 22, in accordance with another preferred embodiment of the present invention. In this preferred embodiment, major axes 63 and 65 of two crystal/foil units 114 and 116 are continuous with the longitudinal axis of the catheter. Unit 114 comprises a piezoelectric crystal 62 which has a resonant frequency, a first foil member 94 coupled to a first side of crystal 62, and a second foil member (not shown) coupled to a second side of crystal 62. Unit 116 comprises a piezoelectric crystal 64 which has a resonant frequency substantially different from that of crystal 62, a first foil member 96 coupled to a first side of crystal 64, and a second foil member (not shown) coupled to a second side of piezoelectric crystal 64. Preferably, the physical dimensions and/or rigidity of the foil members coupled to crystal 62 are accordingly substantially different from those of crystal 64. Using methods described hereinbelow, the ultrasound emissions from crystal/foil units 114 and 116 are distinguished by signal processor 30, and the spatial location of each unit is determined with respect to a reference frame. Calculation of the three-dimensional position coordinates of each of units 114 and 116 determines both the location of the catheter and the orientation of its longitudinal axis.

Figure 3A:
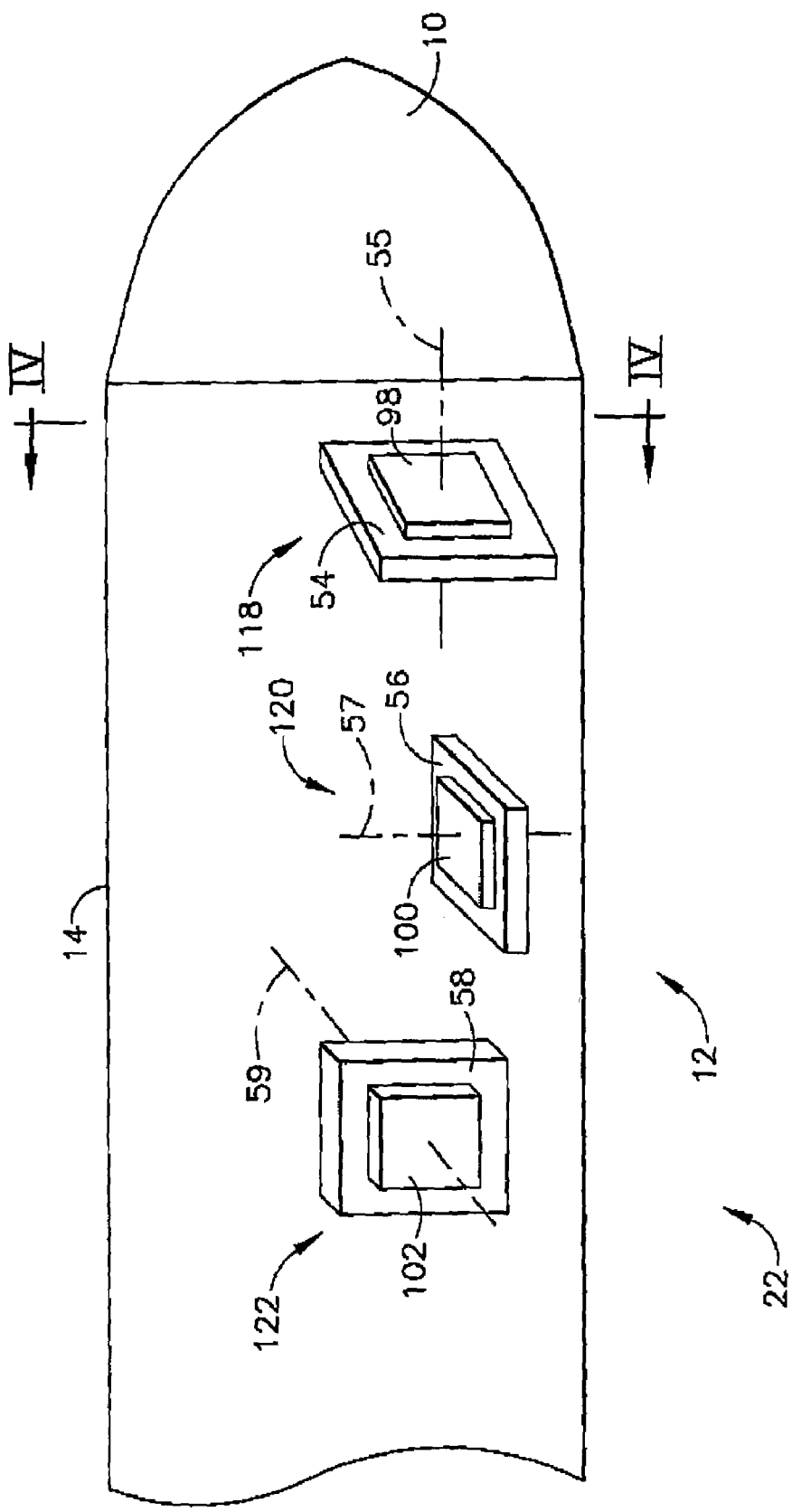
FIG. 3A is a schematic illustration of the distal end of a catheter, for use in the system of FIG. 1, in accordance with another preferred embodiment of the present invention.
Figure 4:
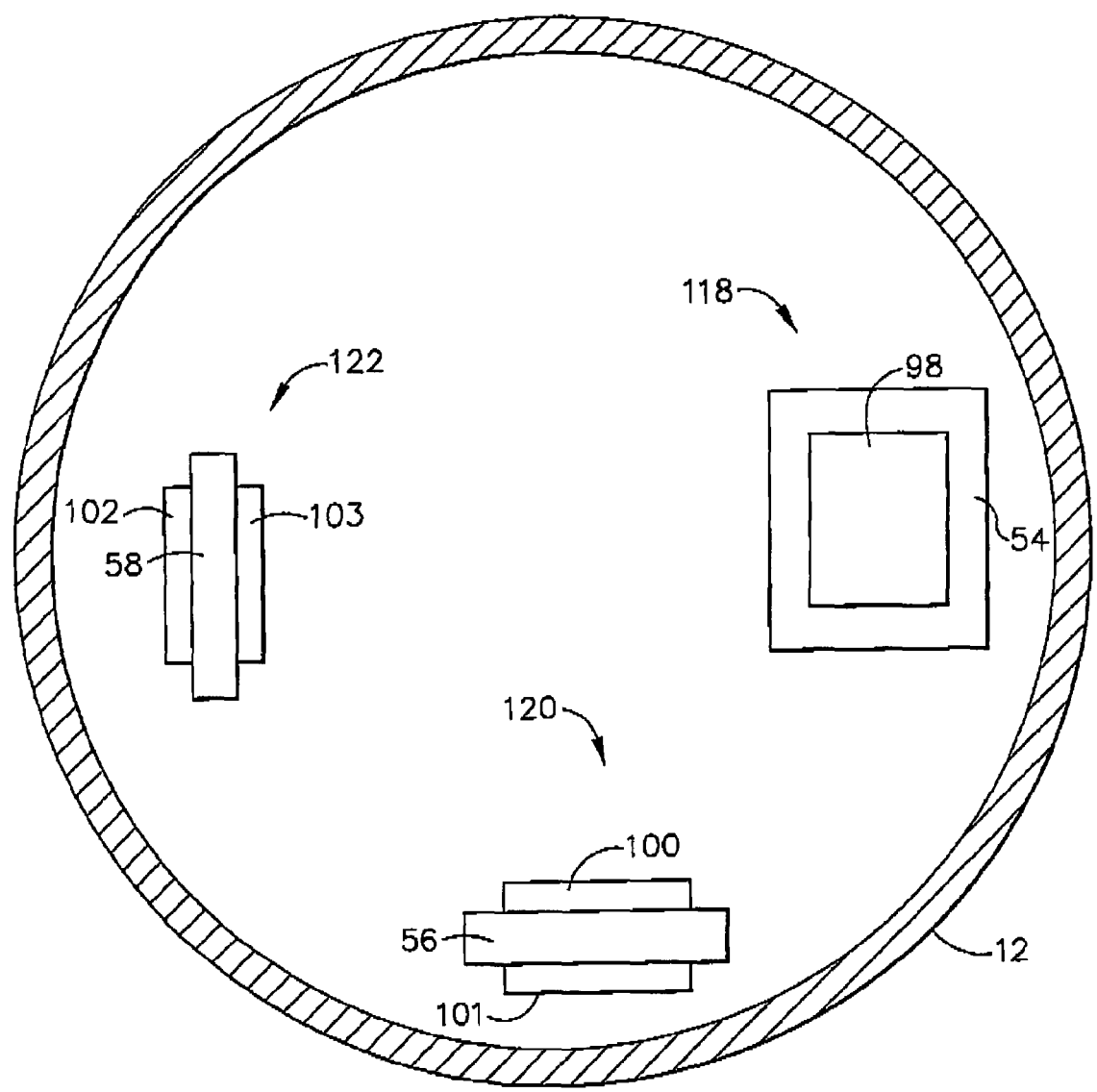
FIG. 4 is a cross-sectional view of the catheter of FIG. 3A.
Figure 5:
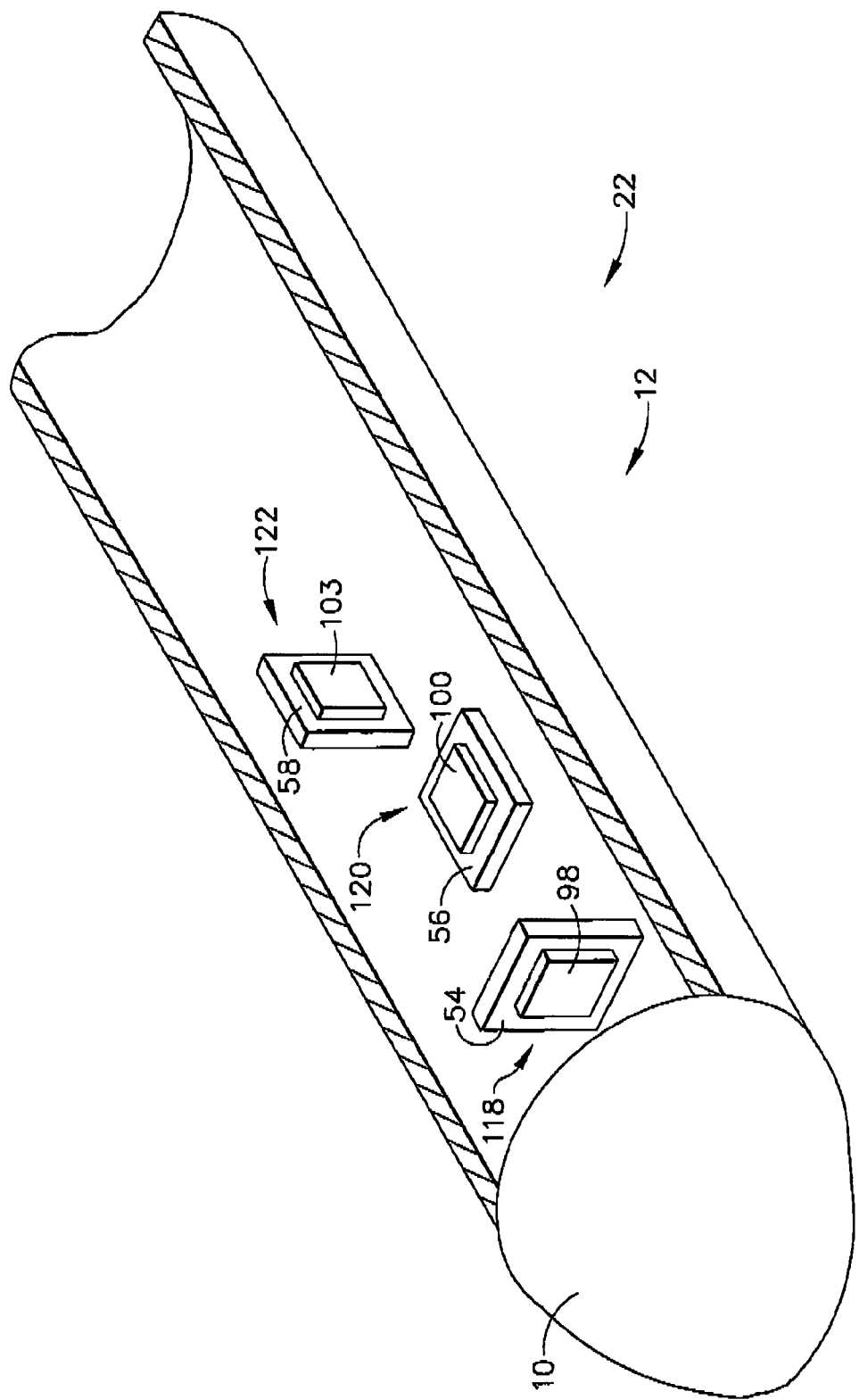
FIG. 5 is a cut-away, simplified pictorial view of the catheter of FIG. 3A.

FIGS. 3A, 4, and 5 are schematic illustrations of the distal end of catheter 22, in side, sectional and isometric views, respectively, in accordance with another preferred embodiment of the present invention. In this preferred embodiment, transducer 12 comprises three crystal/foil units 118, 120, and 122, wherein each unit comprises a piezoelectric crystal and two foil members as described hereinabove. The respective resonant frequencies of units 118, 120, and 122 are substantially different from one another, the different resonant frequencies being attained using methods similar to those used for the embodiment shown in FIG. 2C. Preferably, crystal/foil units 118, 120, and 122 have substantially mutually orthogonal axes 55, 57, and 59, respectively, with axis 55 parallel to but not necessarily collinear with the longitudinal axis of catheter 22. In this embodiment, the differences in one or more aspects of the signals received from any particular crystal/foil unit (e.g. signal strength or signal timing) as detected by detectors 34, 36, and 38, are used to calculate one component of the angular orientation vector of the catheter, as described below.

Figure 3B:
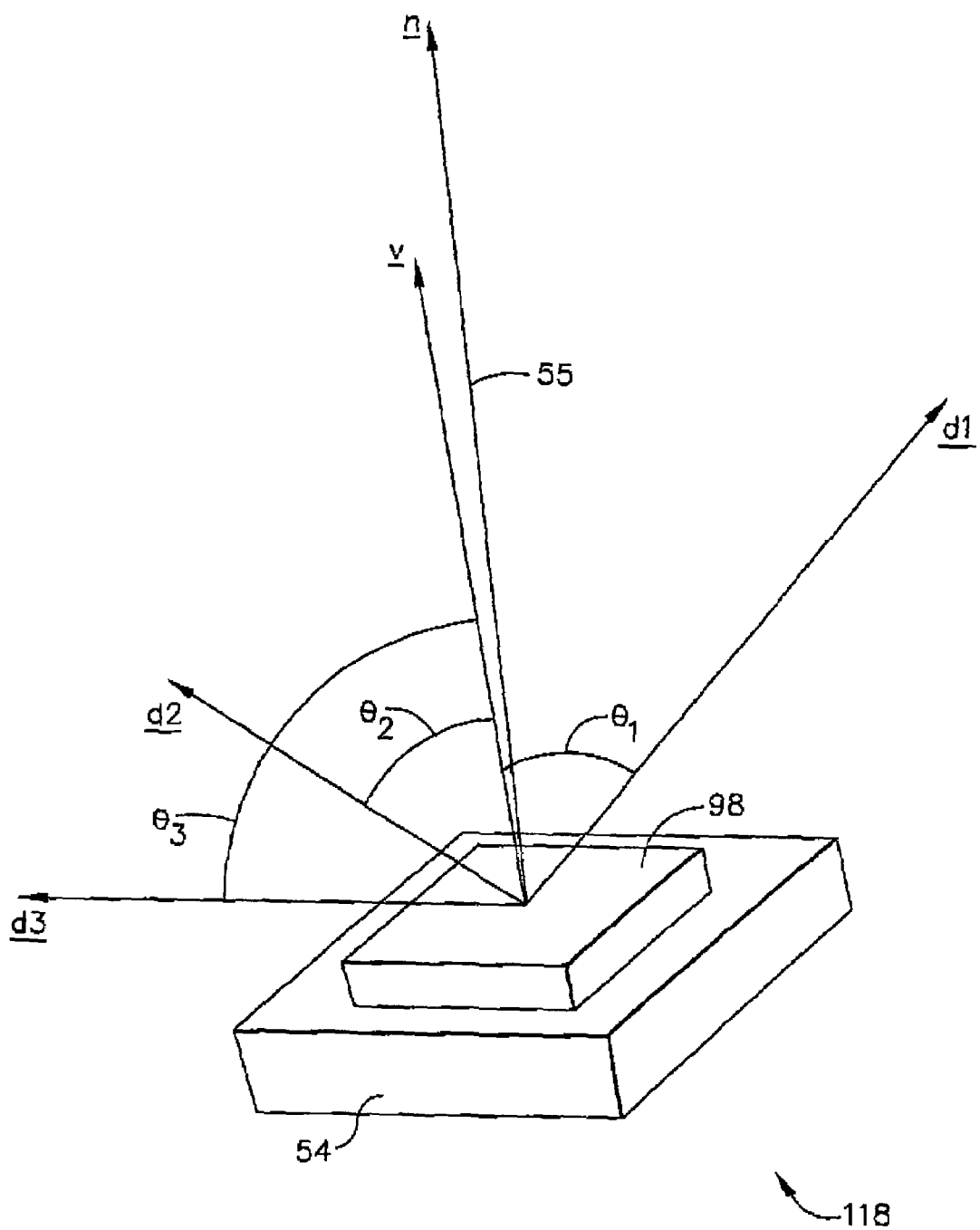
FIG. 3B is a graphical illustration of parameters used in calculating angular coordinates of the catheter shown in FIG. 3A.

FIG. 3B shows parameters according to which the angular orientation of crystal/foil unit 118 in FIG. 3A is calculated from the detected ultrasound waves. In this example, transducer 12 is assumed to be located in tissue whose acoustic properties are substantially homogeneous and isotropic, and wherein emission properties of the crystal/foil unit are such that measurement of the magnitude of acoustic radiation emitted from the unit varies as a function f(i), where i is the angle formed between vectors n and $d_i$, n being orthogonal axis 55 of the unit, and $d_i$ (i=1, 2, or 3) being a vector extending from the center of the unit to one of detectors 34, 36, or 38, respectively. Preferably, the Newton-Raphson method or another multiple iteration algorithm uses the known location of the unit (determined, for example, as described above) and measurements $m_1$, $m_2$, and $m_3$ of the magnitude of the radiation from the unit made by each of the three detectors to find n, the axis of the unit.

The iterative process for finding n preferably comprises guessing an initial vector v, determining the angles 1, 2, and 3 between v and each of the three vectors $d_1$, $d_2$, and $d_3$, and calculating an error function E(v) based on how closely measurements $m_1$, $m_2$, and $m_3$ made at angles 1, 2, and 3 fit f(i). Using methods well known in the art, successive refinements of v yield an estimate substantially equivalent to n, the orthogonal axis of the unit. Execution of this calculation for crystal/foil units 118, 120, and 122 is sufficient to entirely determine the angular orientation of the catheter.

In some preferred embodiments of the present invention, one surface of each crystal/foil unit is coupled to an ultrasound absorber (not shown), which is substantially ultrasound-opaque, in order to substantially attenuate ultrasound radiation emitted in the direction of the absorber. Signal processor 30 integrates the presence of the absorber into calculations determining the angular orientation of the catheter which use the method presented above, in order to distinguish among possible reflected orientations of the catheter that could produce the same detector measurements.

Preferably, as shown in FIG. 4, crystal/foil units 118, 120, and 122 are non-collinear. In this case, by determining the absolute location of three known points on or within a solid object, the angular orientation of the object can also be calculated in place of or in addition to the aforementioned orientation calculation based on the magnitude of the signal emitted from each crystal/foil unit. These two methods can be used together to increase the accuracy and reliability of the calculation of the angular orientation of the catheter.

For most aspects of the present invention, quantitative measurement of the position and/or orientation of the distal end of the catheter 22 relative to a reference frame is necessary. This requires:

at least two non-overlapping crystal/foil units, which generate at least two distinguishable ultrasonic signals, the positions and orientations of the units being known with respect to each other and with respect to the catheter;

at least one RF radiator 40 which generates the field which causes the units to resonate; and at least three non-overlapping, noncollinear detectors 34, 36, and 38, capable of detecting and transducing the time, magnitude, frequency and/or phase information of the ultrasound waves at the fixed points where each of the detectors is located.

In a preferred embodiment of the invention, crystal/foil units 118, 120, and 122 each have a longest dimension of 0.3 mm to 3.0 mm. It will be understood that these dimensions may vary over a considerable range and are only representative of a preferred range of dimensions.

Figure 6:
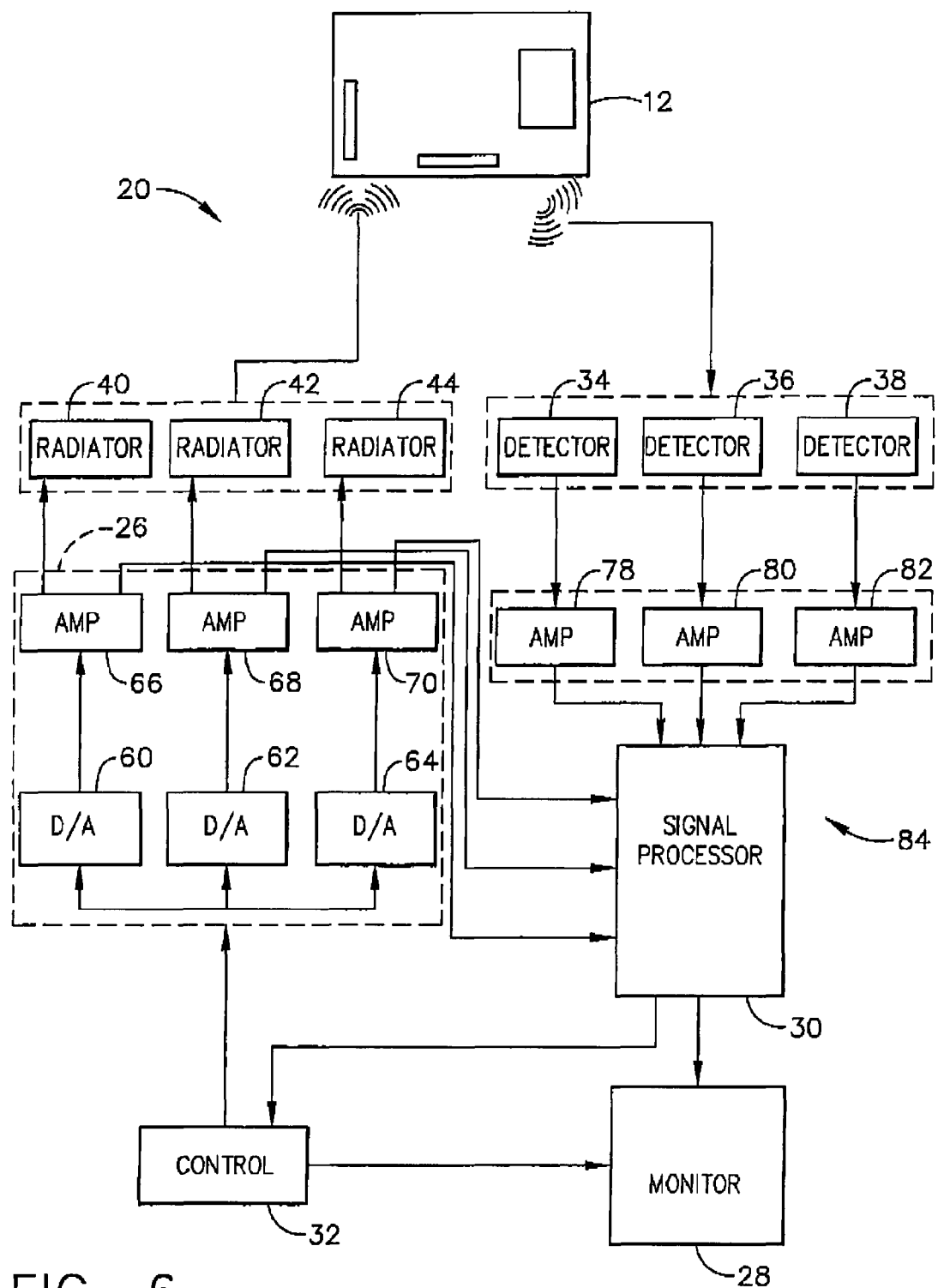
FIG. 6 is a block diagram of circuitry used to determine six-dimensional coordinates of the catheter shown in FIG. 3A, in accordance with a preferred embodiment of the invention.

FIG. 6 is a block diagram showing circuitry 84 used in computing the position of locating transducer 12, in accordance with the preferred embodiment of the present invention shown in FIG. 3A. In this embodiment, RF radiators 40, 42, and 44; crystal/foil units 118, 120, and 122 (shown in FIG.

3A); and detectors 34, 36, and 38 are used to determine the six-dimensional coordinates of locating transducer 12. Control unit 32 utilizes D/A converters 60, 62, and 64 to generate three sine waves of three different frequencies which are input separately to signal amplifiers 66, 68, and 70. RF radiator driver 26, whose output comprises the outputs of amplifiers 66, 68, and 70, generates signals which cause RF radiators 40, 42, and 44 to radiate at frequencies which cause crystal/foil units 118, 120, and 122 respectively to resonate and emit acoustic radiation. Alternatively, one or more of the RF radiators transmit a signal including all of the appropriate frequency components.

The acoustic radiation emitted by each of units 118, 120 and 122 in transducer 12 is detected by each of the detectors, which output signals responsive thereto to amplifiers 78, 80, and 82. The amplifiers then convey amplified signals representing the detected acoustic radiation to signal processor 30. Using methods known in the art, for example a Fast Fourier Transform of the detector signals, signal processor 30 calculates for each detector the components of the signal which are due to each of units 118, 120 and 122. Alternatively, irradiation at the appropriate frequencies occurs in a repeated cycle through each frequency, such that signal processor 30 performs position and orientation calculations for each unit in sequence.

Control unit 32 comprises an assemblage of components to perform intended functions. For example, such components may receive information or signals, process information, function as a controller, display information on a monitor 28, and/or generate information or signals. Typically, control unit 32 comprises one or more microprocessors.

Figure 7:
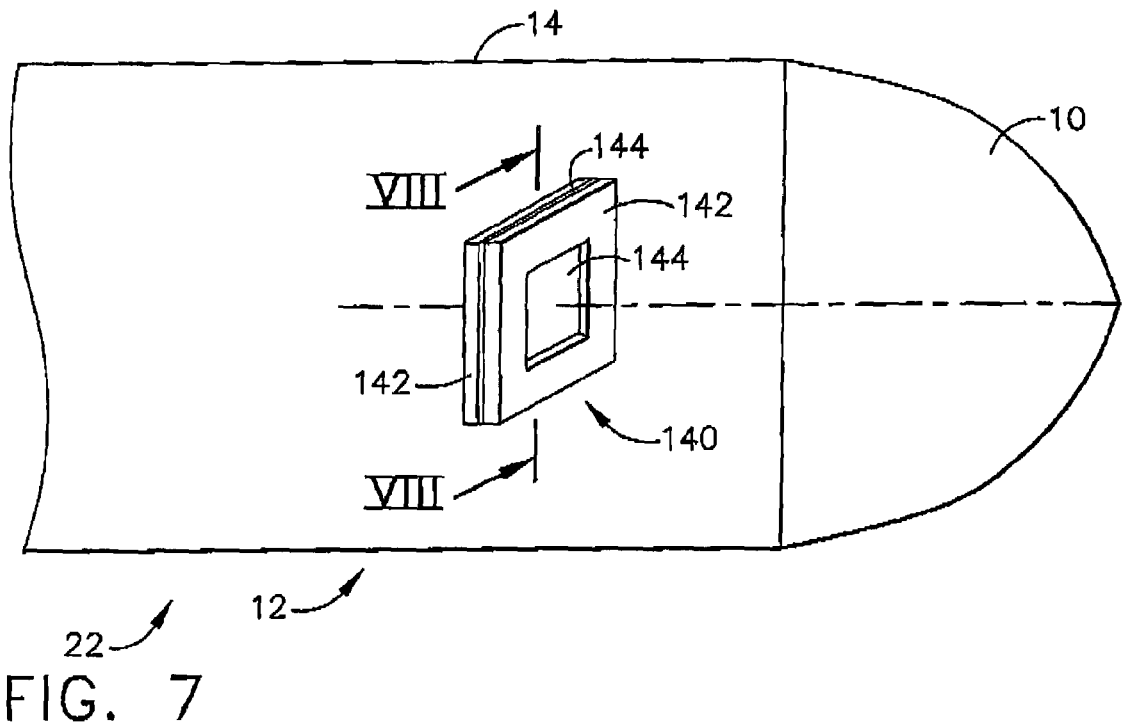
FIG. 7 is a schematic illustration of the distal end of a catheter, for use in the system of FIG. 1, in accordance with another preferred embodiment of the present invention.

FIG. 7 is a schematic illustration of locating transducer 12 which comprises a tag 140, in accordance with another preferred embodiment of the present invention. Tag 140 comprises a diaphragm 144 which has a resonant frequency and a frame 142 which is coupled to a rim of diaphragm 144, so that the diaphragm is firmly mounted and able to vibrate. Preferably, diaphragm 144 comprises a metal film.

Figure 8:
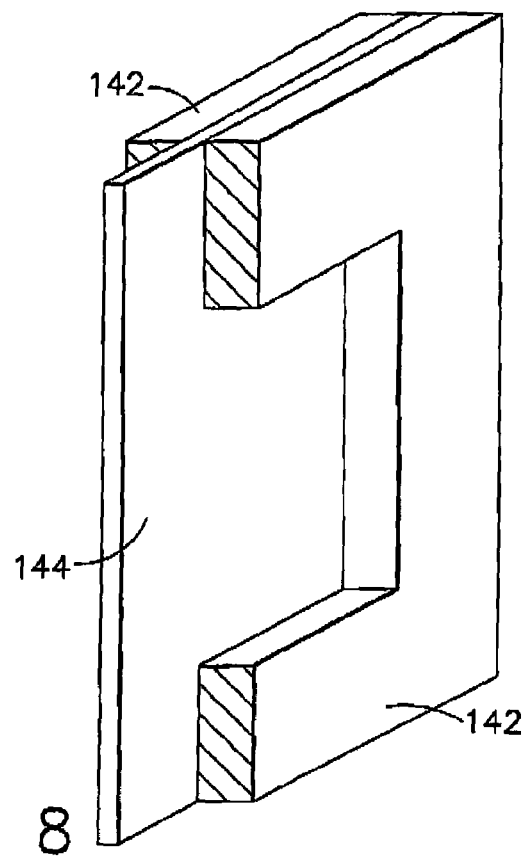
FIG. 8 is a cross-sectional view of a transducer, as used in the distal end of the catheter shown in FIG. 7.

FIG. 8 shows a cross-sectional view of tag 140. Although FIGS. 7 and 8 show one preferred way in which diaphragm 144 may be mounted in frame 142, it will be understood that other arrangements are also possible. For example, in other preferred embodiments (not shown in the figures), one edge of the diaphragm is coupled to the frame, and an opposite edge of the diaphragm is free to vibrate.

Referring again to FIGS. 1 and 7, ultrasound with a frequency substantially similar to the resonant frequency of diaphragm 144 is generated outside of body surface 24 of the patient by ultrasound generator 11 situated at a known location and is directed towards a vicinity of locating transducer 12. The diaphragm mechanically vibrates at its resonant frequency in response to the externally applied ultrasound radiation. RF radiator 40 begins to generate an RF field at a frequency substantially higher than the resonant frequency before or at substantially the same time as the time at which generation of the ultrasound field is initiated. A portion of the RF radiation incident on tag 140 is modulated responsive to the mechanical vibration of the diaphragm. An RF detector 17 located outside of the body surface of the patient detects the RF radiation, and processor 30 separates and detects a modulated RF signal from the unmodulated RF background.

It will be appreciated that although ultrasound generator 11 is shown, for clarity as being a separate unit from detectors 34, 36 and 38, the same type of element may be used for both functions. Similarly, RF detectors 40, 42 and/or 44 may also perform the function of RF detector 17.

The time period starting from the initiation of ultrasound field generation and ending when the modulated RF signal is first detected at the RF detector is substantially the same as the length of time which ultrasound takes to traverse the distance from the ultrasound generator to the diaphragm. Signal processor 30, having inputs corresponding to the externally applied ultrasound and RF fields and the detected RF signal, calculates the distance from the ultrasound generator to the diaphragm based on the measured "time of flight" and the speed of sound in the tissue. Repeating this process using, in sequence, two additional ultrasound generators 13 and 15, located at known points in space, yields the distance from the diaphragm to three known points, and allows the signal processor to calculate the location of the transducer with respect to a reference frame.

Figure 9A:
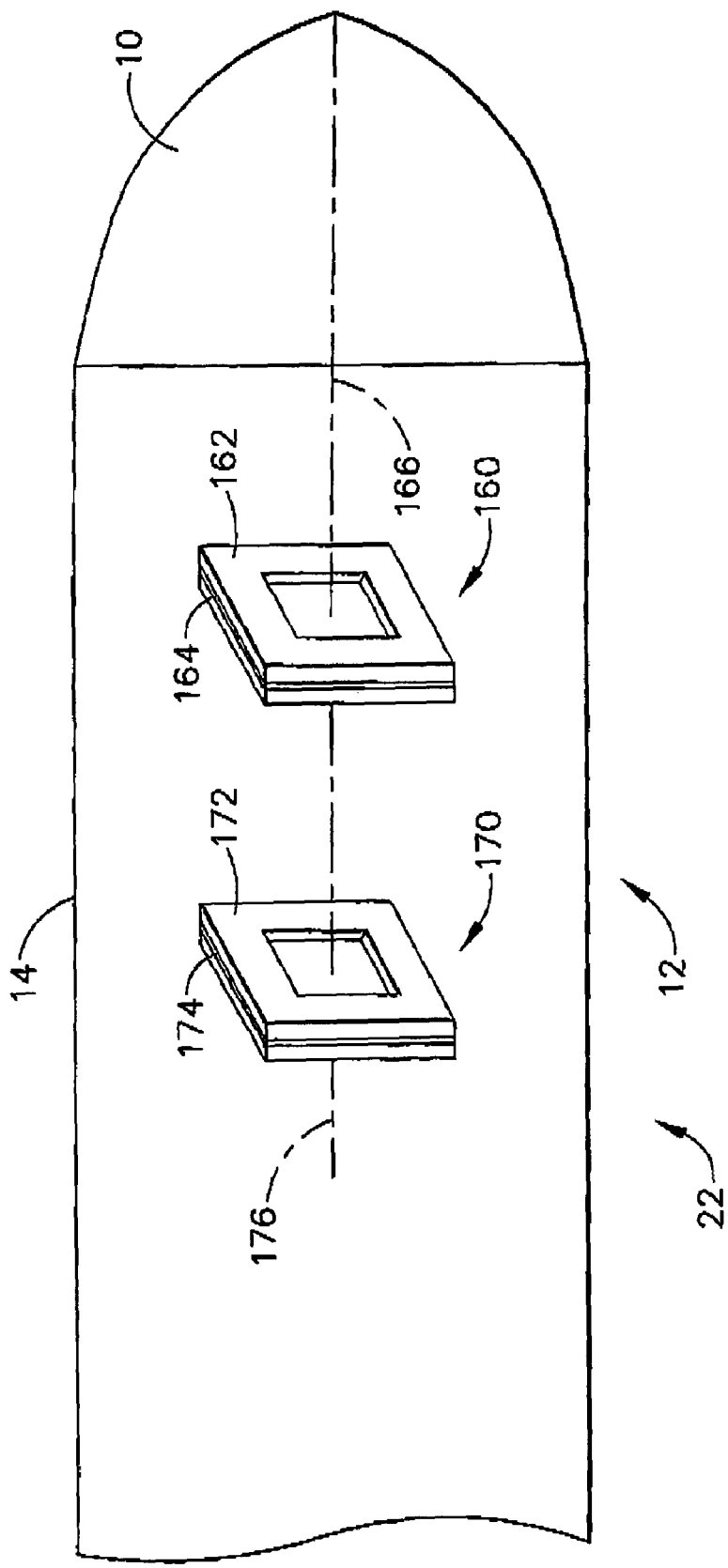
FIG. 9A is a schematic illustration of the distal end of a catheter, for use in the system of FIG. 1, in accordance with another preferred embodiment of the present invention.

FIG. 9A shows a preferred embodiment of the present invention in which locating transducer 12 comprises two tags 160 and 170, axes 166 and 176 of which are generally aligned with the longitudinal axis of the catheter. Tags 160 and 170 comprise diaphragms 164 and 174, respectively, which have different resonant frequencies. Using methods similar to those described above, the location of each diaphragm is calculated, and the angular orientation of the longitudinal axis of the catheter is thereby determined.

Figure 9B:
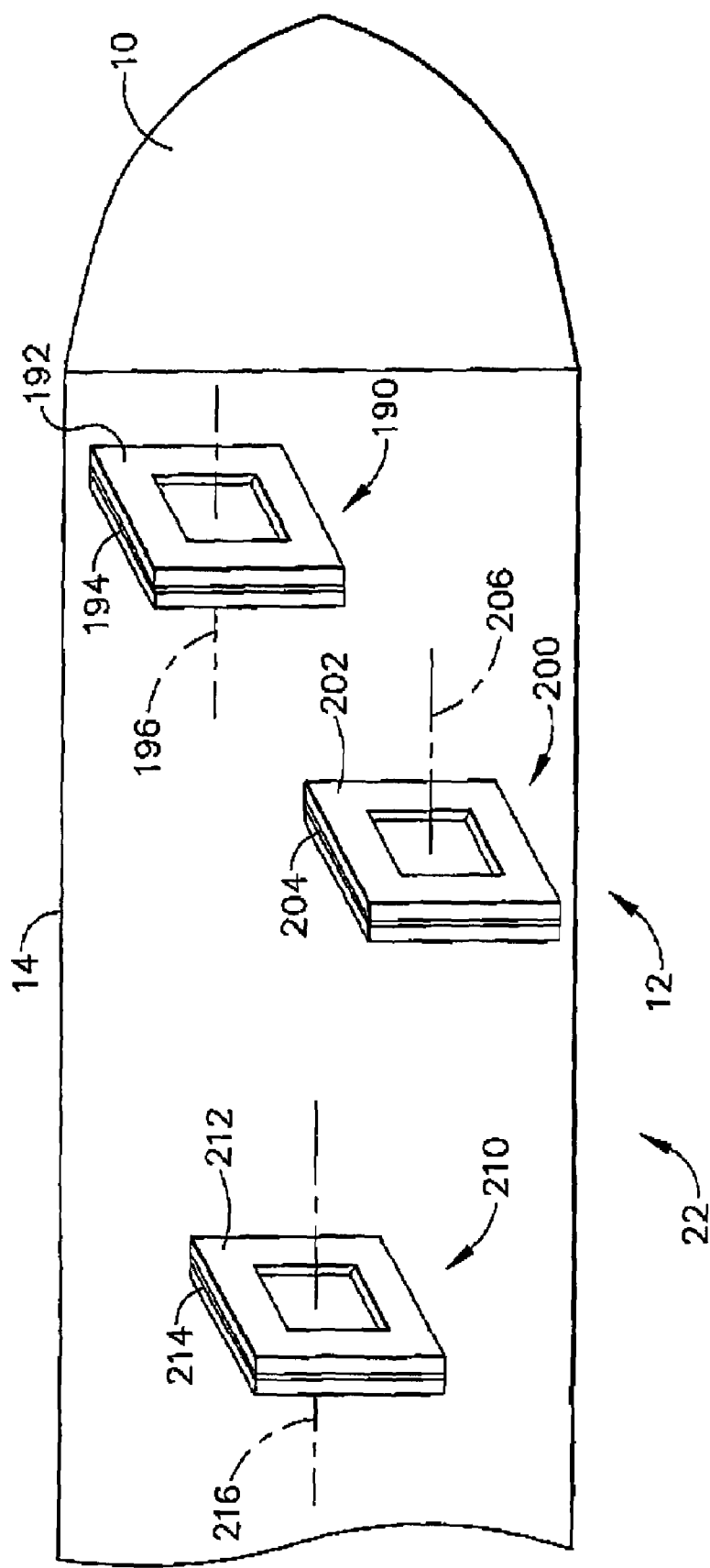
FIG. 9B is a schematic illustration of the distal end of a catheter, for use in the system of FIG. 1, in accordance with yet another preferred embodiment of the present invention.

FIG. 9B shows a schematic illustration of another preferred embodiment of the present invention, in which locating transducer 12 comprises three non-collinear tags 190, 200, and 210 fixed at known positions to the transducer. Tags 190, 200, and 210 comprise diaphragms 194, 204, and 214, respectively, each diaphragm having a substantially different resonant frequency from that of the other diaphragms. In this embodiment, the location of each diaphragm is found using the procedure described above, this calculation thereby yielding the angular orientation of the transducer.

Although preferred embodiments are described hereinabove with reference to a catheter, it will be understood that the principles of the present invention may be used in position and/or orientation detection of other types of objects, as well. The preferred embodiments are cited by way of example, and the full scope of the invention is limited only by the claims.

The invention claimed is:

1. Apparatus for determining the disposition of an object relative to a reference frame, comprising:
   at least one field generator, which generates an electromagnetic field in a vicinity of the object;
   at least one transducer, which is fixed to the object and which vibrates at a predetermined vibrational frequency and emits energy, responsive to an interaction of the electromagnetic field therewith;
   one or more detectors in a vicinity of the object which detect the energy emitted by the transducer and generate signals in response thereto;
   a signal processor which receives and processes the detector signals to determine coordinates of the object, the signal processor calculating the position and/or orientation of the at least one transducer by determining three position vector components and three components of angular orientation; and
   a display for displaying the position and/or orientation of the at least one transducer.

2. Apparatus according to claim 1, wherein there is substantially no wired connection to the transducer.

3. Apparatus according to claim 1, wherein the signal processor processes the detector signals to determine a time of flight of acoustic energy indicative of a distance of the transducer from at least one known point in the reference frame.

4. Apparatus according to claim 3, wherein the at least one transducer comprises two or more transducers, which vibrate at substantially different respective frequencies, and wherein the signal processor processes the detector signals responsive to the different frequencies.

5. Apparatus according to claim 4, wherein the signal processor determines the distance from the at least one fixed point to the two or more transducers in order to determine an angular orientation of the object.

6. Apparatus according to claim 1, and comprising one or more ultrasound generators which emit ultrasound at frequencies substantially similar to the frequency of the transducer, in order to cause the transducer to vibrate.

7. Apparatus according to claim 1, wherein the one or more detectors detect a modulation of the electromagnetic field responsive to vibration of the transducer.

8. Apparatus according to claim 1, wherein the at least one field generator comprises one or more radio frequency (RF) field generators, and wherein the one or more transducers vibrate and emit ultrasound radiation responsive to the RF field.

9. Apparatus according to claim 8, wherein the one or more detectors comprise a plurality of ultrasound detectors, situated at known locations in the reference frame, which receive the ultrasound radiation emitted by the one or more transducers.

10. Apparatus according to claim 8, wherein the one or more transducers comprise a plurality of transducers having different, respective frequencies, and wherein RF field generators generate fields at different, respective frequencies, corresponding to the different frequencies of the transducers.

11. Apparatus according to claim 10, wherein the at least one transducer comprises two or more transducers which are oriented relative to the object at substantially different respective angular orientations, and wherein the signal processor determines angular orientation coordinates of the object responsive to a difference in the energy emitted by the two or more transducers.

12. Apparatus according to claim 1, wherein the object comprises an invasive medical instrument, and wherein the signal processor determines coordinates of the instrument inside the body of a subject.

13. Apparatus according to claim 12, wherein the medical instrument comprises a probe having a physiological sensor fixed to a distal portion thereof, in proximity to the at least one transducer.

14. Apparatus for determining the disposition of an object relative to a reference frame, comprising:
at least one field generator, which generates an electromagnetic field in a vicinity of the object;
a transducer, fixed to the object, which emits acoustic energy responsive to the electromagnetic field;
one or more detectors at known positions in a vicinity of the object, which detect the acoustic energy emitted by the transducer and generate signals in response thereto;
a signal processor which receives and processes the detector signals to determine coordinates of the object, the signal processor calculating the position and/or orientation of the at least one transducer by determining three position vector components and three components of angular orientation; and
a display for displaying the position and/or orientation of the at least one transducer.

15. Apparatus according to claim 14, wherein the transducer emits the acoustic energy substantially irrespective of any acoustic irradiation of the object.

16. Apparatus according to claim 14, wherein there is substantially no wired connection to the transducer.

17. Apparatus according to claim 14, wherein the signal processor determines a time of flight of the acoustic energy from the transducer to the one or more detectors.

18. Apparatus according to claim 17, wherein the time of flight comprises a time interval between an initiation of the electromagnetic field by the at least one field generator to an initial detection of the acoustic energy by the one or more detectors.

19. A method for determining the disposition of an object relative to a reference frame, comprising:
fixing to the object a transducer, which vibrates at a vibrational frequency thereof;
generating an electromagnetic field in a vicinity of the object;
detecting energy, emitted by the transducer responsive to an interaction of the field with the transducer, the energy having a frequency dependent on the vibrational frequency of the transducer, at one or more locations in the reference frame and generating signals responsive thereto;
processing the signals to determine coordinates of the object based on three vector components and three components of angular orientation; and
displaying the position and/or orientation of the transducer.

20. A method according to claim 19, wherein processing the signals comprises determining a time of flight of acoustic energy indicative of a distance of the transducer to at least one known point in the reference frame.

21. A method according to claim 20, wherein fixing a transducer to the object comprises fixing at least two transducers to the object, which vibrate at substantially different resonant frequencies.

22. A method according to claim 21, wherein processing the signals comprises determining a distance from the at least one fixed point to each of the at least two transducers in order to determine an angular orientation of the object.

23. A method according to claim 20, and comprising generating one or more ultrasound fields, at frequencies substantially similar to the resonant frequency of the transducer, in order to cause the transducer to vibrate.

24. A method according to claim 20, wherein detecting the energy comprises detecting a modulation of the electromagnetic field responsive to vibration of the transducer.

25. A method according to claim 20, wherein generating an electromagnetic field comprises generating a radio frequency (RF) field, and wherein detecting the energy comprises detecting acoustic radiation emitted by the transducer responsive to the RF field.

26. A method according to claim 25, wherein processing the signals comprises determining, for a plurality of known locations in the reference frame, a time of flight to each of the locations of the ultrasound radiation emitted by the transducer.

27. A method according to claim 26, wherein fixing a transducer to the object comprises fixing two or more transducers to the object at substantially different respective angular orientations, each of which vibrates at a substantially different respective resonant frequency, and
wherein generating an RF field comprises generating a field comprising frequency components corresponding to the respective resonant frequencies of the two or more transducers, and wherein processing the signals comprises comparing signals generated responsive to the acoustic radiation detected at the different frequencies to determine an angular orientation of the object.

28. A method according to claim 19, wherein determining the disposition of an object comprises determining the disposition of an invasive medical instrument.

29. A method according to claim 28, wherein determining the disposition of the invasive medical instrument comprises determining the disposition of an invasive medical instrument with a physiological sensor fixed to a distal portion thereof, in proximity to the transducer.

\* \* \* \* \*